United States Patent [19]

Lock

[11] Patent Number: 4,625,720

[45] Date of Patent: Dec. 2, 1986

[54] WOUND DRESSING MATERIAL

[76] Inventor: Peter M. Lock, Raniganj, Bowesden Lane, Shorne, Nr. Gravesend, Kent, England

[21] Appl. No.: 572,307

[22] Filed: Jan. 20, 1984

[51] Int. Cl.[4] ............................................. A61L 15/00
[52] U.S. Cl. ............................... 128/156; 128/132 D; 128/155; 521/51; 521/61; 521/128
[58] Field of Search ................... 128/155, 156, 132 D; 521/51, 61, 128

[56] References Cited

U.S. PATENT DOCUMENTS

| | | | |
|---|---|---|---|
| 3,113,568 | 12/1963 | Robins | 128/156 |
| 3,476,933 | 11/1969 | Mendelsohn | 521/61 |
| 3,978,855 | 9/1976 | McRae et al. | 128/156 |
| 4,048,105 | 9/1977 | Salisbury | 521/51 |
| 4,186,255 | 1/1980 | Klein et al. | 521/128 |
| 4,233,969 | 11/1980 | Lock et al. | 128/156 |
| 4,292,411 | 9/1981 | Jourquin et al. | 521/51 |

OTHER PUBLICATIONS

*The Merck Index*, Tenth Edition, 1983 p. 1364 Formulae 9358 and 9357.

*Primary Examiner*—C. Fred Rosenbaum
*Assistant Examiner*—Jerome R. Smith, Jr.
*Attorney, Agent, or Firm*—Birch, Stewart, Kolasch & Birch

[57] ABSTRACT

A wound dressing material comprising a sheet of a synthetic plastics material which is permeable to water vapour and to air, having on one side a surface for application to a wound, and immediately behind the said surface a cellular region having a structure of collapsed, open cells which intercommunicate with one another, and a more dense region behind the cellular region, and an intermediate region in which there is a gradual transition from the cellular region to the more dense region, so that on contact with liquid exudate from a wound, the dressing material will absorb a limited amount of exudate into the cellular region but prevent it from passing right through the dressing material.

18 Claims, 1 Drawing Figure

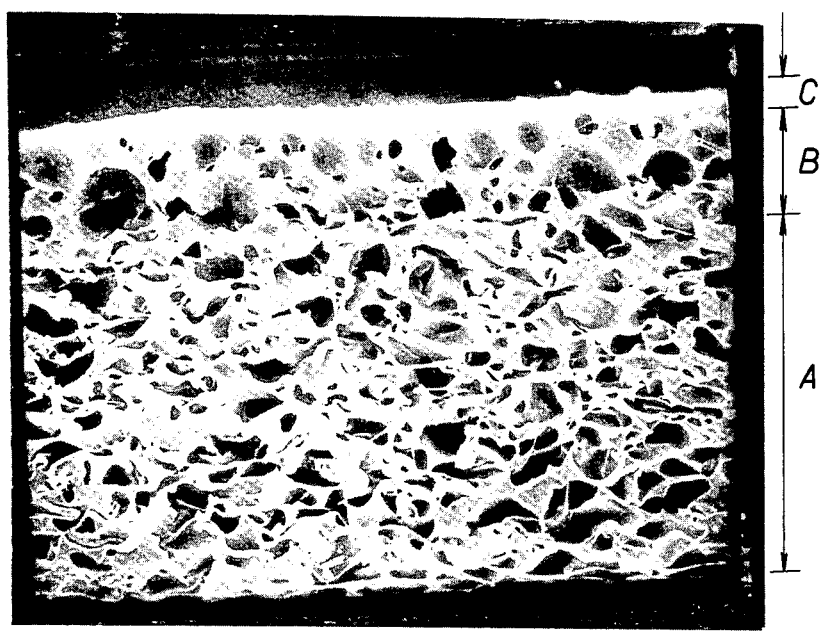

WOUND DRESSING MATERIAL

This invention relates to wound dressing materials, and more specifically to a material which can be applied to many types of injury or wound but is particularly useful as a temporary wound cover in the therapeutic treatment of burns, varicose ulcers, pressure areas and other related injuries. The term "burns" covers thermal, chemical, electrical and similarly inflicted wounds involving skin damage or destruction.

Burns require a unique combination of therapy and dressing when the function of the skin is absent or impaired, because nutritious body fluids and their essential components are continuously lost through the wound, which in the case of a large area burn can cause dehydration of the patient and in turn involve more series complications such as lung and kidney malfunctions, while the normal protection provided by the skin from invading harmful bacteria and other toxic and noxious agents is no longer available.

Many types of dressing material having been used heretofore. Absorbent fibrous materials such as cotton gauze can cause excessive dehydration and drying of the wound and thus become firmly adhered to the affected area, so that dressing changes are painful and can cause further damage to the wound. The natural healing process in which skin cells multiply and migrate across the moist wound surface is delayed, because the cells have to burrow deep under the dried area. Individual fibres can also become detached from the dressing and embedded in the wound and thereby impede healing.

To prevent adherence and maintain a moist wound environment, dressing materials impregnated with greasy substances such as petroleum jelly have been employed. These dressings require frequent changing to avoid drying out, with consequent frequent exposure of the wound to airborne bacteria, and the greasy substances provide a good environment for the proliferation of bacteria so that wound infection is difficult to avoid, while the greasy substances can also be absorbed into the would and retard healing by acting as foreign bodies.

Dressings made of polyethylene, polypropylene and polyamide films eliminate adherence of the dressing to the wound and prevent particles being embedded therein, but being non-porous they cannot absorb the excess of liquid exudate which exudes from a burn and they can therefore become painful to the patient unless changed frequently, with consequent exposure of the wound to airborne bacteria. The micro-climate under such film dressings, while favourable for healing, is also ideal for such bacteria so that wound infection again becomes a problem, while the fact that the condition of the would is visible through the film dressing is depressing to the patient. Other film dressing materials made of gelatins, alginates and celluloses have been designed to create the same favourable micro-climate in the wound by dissolving or melting in the exudate and re-forming as part of the eschar (scab). This increases would dehydration and the films, when mixed with the exudate in the eschar, become supportive of bacteria but cannot be removed from the wound because they have become an integral part of it. Even if infection is avoided, the dehydration effect delays healing. Plastic spray-on dressings involve similar problems, particularly encapsulation of dressing material deep in the wound.

Absorbent dressings of polyvinyl alcohol sponge and of polyurethane foam with an open cell structure have been found to cause wound dehydration and adherence of the dressing to the wound, while small particles of the cells of the dressing material can become detached and embedded in the wound, causing undesirable reactions. Also, passage of the exudate right through the dressing can provide a nutrient path for airborne bacteria back through the dressing into the wound. A polyurethane foam dressing with an impermeable backing of polytetrafluoroethylene avoids the latter problem but still suffers from the problem of detached particles.

Biological wound covers, mainly of porcine and cadaver skin, perform well in many respects but suffer from the problem that it is extremely difficult to avoid leaving small fragments to dermis in the wound when removing the dressing, producing subsequent foreign body reactions which can cause rejection of autografts and later breakdown of healed wounds, and causing production of antibodies which might involve serious consequences at a later date.

In British Pat. No. 1562244 I have described a wound dressing material which is free from the disadvantages of the known materials described above, and which comprises a sheet of a synthetic plastics material which is permeable to water vapour and to air, having on one side a smooth glazed surface for application to a wound, a cellular region behind the smooth surface, the cells in the cellular region being closed cells, and a more dense region behind the other surface, so that on contact with liquid exudate from a wound the dressing material will absorb a limited amount of exudate but prevent it from passing right through the dressing material.

The fact that the dressing material is water vapour- and air-permeable, but will not permit the liquid exudate to pass through it, assists in maintaining a moist micro-climate favourable for healing in the wound. The smooth glazed surface avoids the danger of detachment of cell particles and assists in preventing adherence of the dressing to the wound. The cellular region enables the dressing to absorb excess of liquid exudate without drawing out so much exudate that the wound would become dried and the patient dehydrated. Dressings need not be changed too frequently.

Although this wound dressing material is very successful and is a substantial improvement over the known materials described above, in certain circumstances it has a slight disadvantage in that it is not sufficiently pliable to conform closely to the wound area to be protected and has to be maintained in position by application of additional dressings and/or adhesive tapes. I have now found an alternative wound dressing material which provides all the advantages of my earlier wound dressing material, and which is, in addition, exceedingly pliable and therefore will readily conform to the surface of a wound to be dressed.

Accordingly the present invention provides a wound dressing material comprising a sheet of a synthetic plastics material which is permeable to water vapour and to air, having on one side a surface for application to a wound, and immediately behind the said surface a cellular region having a structure of collapsed, open cells which intercommunicate with one another, and a more dense region behind the cellular region, and an intermediate region in which there is a gradual transition from the celluloar region to the more dense region, so that on contact with liquid exudate from a wound, the dressing material will absorb a limited amount of exudate into the cellular region but prevent it from passing right through the dressing material.

The physical structure of a wound dressing material in accordance with the present invention is illustrated in the accompanying drawing which shows a photograph of a transverse cross-section of a material in accordance with the invention magnified 85 times.

Preferably the synthetic plastics material is a polyurethane, in particular the product of polymerisation of a polyoxyethylene polyol with a polyisocyanate in the presence of a cross-linking agent or catalyst which is reactive with the isocyanate groups, the polymerisation being performed without any substantial amount of water present.

The preferred catalyst is dimethylethanolamine. The cross-linking agent preferably contains in its molecule two or more amine and/or hydroxyl groups which are reactive with the isocyanate groups.

In a preferred embodiment, the polyol is a polyoxyethylene diol having a weight average molecular weight of approximately 3000. In a particularly preferred embodiment the wound dressing material is prepared from a formulation comprising the following composition by weight:

Polyoxyethylene glycol (m.wt. 3000): 100 parts
Dimethylethanolamine: 0.1-1.0 parts
Silicone oil: 1-10 parts
Toluene di-isocyanate: 25-50 parts The invention also comprehends a method of making a wound dressing material, comprising the steps of mixing a polyoxyethylene polyol with a polyisocyanate and, if desired, a surfactant with agitation to form an aerated creamy mix, incorporating a cross-linking agent or catalyst in the mix, spreading the mix on to a smooth glazed release paper to form a sheet of a predetermined uniform thickness, and allowing the mix to polymerise at a temperature not higher than 25° C., preferably below 10° C., with the exclusion of any substantial amount of water from the mix during the said steps. Preferably the release paper is supported on a flat surface, such as a sheet of glass, during the spreading and polymerising steps. The spreading may be effected by means of at least one spreader bar with a corrugated surface which is drawn over the surface of the paper at a fixed distance above it. The curing is preferably effected in a curing cabinet in which a force draught of refrigerated, anhydrous air is passed over the upper surface of the sheet.

The present invention will now be illustrated by the following Examples.

EXAMPLE 1

In a preferred embodiment of the invention, the dressing material is formed by polymerisation of a polyethyleneglycol supplied by Union Carbide under the Trade Name NYAX, and having an average molecular weight of approximately 3000, with a toluene di-isocyanate supplied by Lankro Chemicals and having an Index of 109.

Thus 100 parts by weight of NYAX polyol are mixed with 1-10 parts by weight, preferably 4 parts by weight, of silicone oil (L-620; supplied by Union Carbide) to form an aerated creamy mix at a temperature of 22°-25° C. Subsequently, 25-50 parts by weight, preferably 45 parts by weight, of toluene di-isocyanate having an Index of 109 (supplied by Lankro Chemicals), are blended into the mix to form a cream. Then, 0.1-1.0, preferably 0.5 parts, of dimethylethanolamine (sold as Propamine A by Lankro Chemicals) is mixed into the blended mix as quickly as possible.

The creamed mixture is then poured on to a smooth glazed release paper which is tightly stretched over a long table having a flat surface, such as a sheet of smooth plate glass, to ensure absence of wrinkles, folds, or ridges. The creamy mix is then spread over the paper to form a layer of uniform thickness, usually 0.5 mm thick.

The coated paper is then placed on trays which are transferred to a curing cabinet through which a current of dry, cooled air is circulated while curing of the mix takes place.

The mixing and polymerisation processes are performed in conditions which are as anhydrous as possible. Thus, the mixing of the reactants is performed in conditions of minimum relative humidity and the air passing into the curing cabinet is dried by passing it through silica gel. The temperature in the curing cabinet is preferably maintained below 10° C., or even lower by refrigerating the air which enters into the curing cabinet.

Under these conditions it is found that the volume of the creamy mix begins to increase about five minutes after the catalyst Propamine A has been added. As the mix cures it continues to rise for about a further 30 minutes to 1 hour. Thereafter, the layer beings to "deflate" and after a further 3 hours it has fallen to a level comparable with its original thickness.

EXAMPLE 2

A wound dressing material in accordance with the present invention is prepared in the same manner as described in Example 1 and using the same formulation as described in Example 1 but incorporating additionally the following ingredients:

| | |
|---|---|
| Stannous octoate (supplied by Durham Raw Materials under the Trade Name NEVOCURE) | 1–10 parts by weight preferably 4 parts by weight |
| Trichlorofluoromethane | 5–20 parts by weight, preferably 9 parts by weight |

It is believed that the process used to prepare the wound dressing material of the present invention causes the initial formation of a "foamed" region in the layer of polymerising materials, which foamed region consists of open cells which communicate with one another. On completion of curing, a non-rigid structure is obtained which "collapses" as air escapes from the intercommunicating cells through the outer surface of the cured polymer.

Curing and subsequent "collapse" of the material is usually completed in approximately four hours. The dressing material, still with its release paper backing, is cut into the required shapes and sizes for a medical/surgical wound cover by means of a band knife or roller press and is wrapped in a siliconised tissue and packaged in foil pouches which are sealed and gamma-irradiated to ensure sterile conditions.

A typical transverse cross-section of a sheet of wound dressing material in accordance with the present invention is illustrated in the accompanying drawing which is a photograph of 85 times magnification. The photograph shows a first region A of the collapsed, open cells which intercommunicate with one another, and the more dense region C behind the cellular region, with an intermediate region B in which there is a gradual transition from the cellular region A to the more dense region C. In use, the lower surface of cellular region A as illustrated is applied to the wound to be healed.

Tests have shown that the polymerized dressing material is free from toxic cyanate or amine residues and is highly effective as a wound cover in the treatment of burns. On application to a burn, it conforms to the contour of the wound and absorbs a limited amount of the liquid exudate, while swelling slightly. It is believed that this swelling on contact with liquid causes the cells to open to receive liquid.

In addition to the advantages mentioned above, the dressing material has the specific advantages of resembling skin in texture, of conforming easily and readily to any anatomical contour, and of causing no pain in application. It also has thermal insulation qualities which enable it to maintain an optimum temperature in the wound to promote healing. It is permeable to water vapour and air, so as to permit the passage of gases through it, but being impermeable to liquids it prevents drying and dehydration in or around the wound area. It is non-adherent to wounds, making for painless dressing changes. It does not distort or impede X-ray examination. It is unaffected by contact with antiseptics, and under slight pressure it can act as a haemostat. It will not support bacterial life or growth and it produces no loose fibres or particles which could become embedded or encapsulated in a wound. It requires no soaking before use as with biological wound covers, thus saving valuable nursing time, and it can be applied by any trained nurse without specialised training. The risk of infection is reduced because of the relatively infrequent dressing changes required, and the similarity of skin in texture has a good psychological effect on the patient. The production of a correct micro-climate in the wound increases the speed of healing.

What is claimed is:

1. A wound dressing material comprising a sheet of a synthetic plastics material which is permeable to water vapour and to air, having on one side a surface for application to a wound, and immediately behind the said surface a low density cellular region having a structure of collapsed, open cells which intercommunicate with one another, and a more dense region behind the cellular region, and an intermediate region in which there is a gradual transition from the cellular region to the more dense region, so that on contact with liquid exudate from a wound, the dressing material will absorb a limited amount of exudate into the cellular region but prevent it from passing right through the dressing material.

2. A wound dressing material according to claim 1, wherein the synthetic plastics material is polyurethane.

3. A wound dressing material according to claim 2, wherein the synthetic plastics material is the product of polymerisation of a polyoxyethylene polyol with a polyisocyanate in the presence of a cross-linking agent or catalyst which is reactive with the isocyanate groups, without any substantial amount of water present.

4. A wound dressing material according to claim 3, wherein the cross-linking agent or catalyst contains in its molecule two or more amine and/or hydroxyl groups which are reactive with the isocyanate groups.

5. A wound dressing material according to claim 3, wherein the catalyst is dimethylethanolamine.

6. A wound dressing material according to claim 3, wherein the polyol is a polyoxyethylene glycol having a weight average molecular weight of approximately 3000.

7. A wound dressing material according to claim 3, wherein the polyisocyanate is toluene di-isocyanate.

8. A wound dressing material according to claim 1, and which has been prepared from a formulation comprising the following composition by weight:
   Polyoxyethylene glycol (m.wt 3500): 100 parts
   Dimethylethanolamine: 0.1–1.0 parts
   Silicone oil: 1–10 parts
   Toluene di-isocyanate: 25–50 parts 9. A wound dressing material according to claim 1, which is prepared by a process comprising the steps of mixing a polyoxyethylene polyol with a polyisocyanate and, if desired, a surfactant with agitation to form an aerated creamy mix, incorporating a catalyst which is reactive with the isocyanate groups or a cross-linking agent in the mix, spreading the mix onto a smooth glazed release paper to form a sheet of a predetermined uniform thickness, and allowing the mix to polymerize at a temperature not higher than 25° C., with the exclusion of any substantial amount of water from the mix during the said steps.

10. A method for treating wounds, which comprises: applying to a wound said side surface of the wound dressing material of claim 1.

11. A sterile wound dressing material comprising a pliable sheet of a synthetic plastics material which is permeable to water vapor and to air and impermeable to liquids, having on one side a surface for application to a wound, and immediately behind the said surface a low density collapsed cellular region having a structure of collapsed, open cells which intercommunicate with one another, and a more dense region behind the ceullular region, and an intermediate region in which there is a gradual transition from the collapsed cellular region to the more dense region, so that on contact with liquid exudate from a wound, the collapsed cellular region of the dressing material will expand and absorb a limited amount of exudate but the dense region will prevent the exudate from passing right through the dressing material.

12. A wound dressing material according to claim 11, and further comprising a smooth glazed release paper applied to said surface for application to a wound.

13. A wound dressing material according to claim 11, which is free from toxic cyanate or amine residues.

14. A method for treating wounds which comprises applying to a wound said side surface of the wound dressing material of claim 11.

15. A sterile wound dressing material according to claim 1, which is made by a process comprising the steps of mixing a polyoxyethylene polyol with a polyisocyanate to form a aerated creamy mix, spreading the mix onto a smooth glazed release paper to form a sheet of a predetermined uniform thickness, curing the sheet under substantially anhydrous conditions at a temperature below 10° C., thereby allowing the sheet to rise and cure to form a non-rigid foamed region which consists of open cells which communicate with one another and allowing the foamed region to collapse.

16. A sterile wound dressing material comprising a pliable sheet of a synthetic plastics material which is permeable to water vapor and to air and impermeable to liquids, having on one side a surface for application to a wound, and immediately behind said surface a low density collapsed cellular region which constitutes the majority of the cross-sectional area of the sheet, said collapsed cellular region having a structure of collapsed, open cells which intercommunicate with one another, and a more dense region behind the cellular region, and an intermediate cellular region in which there is a gradual transition from the collapsed cellular region to the more dense region, so that on contact with liquid exudate from a wound, the collapsed cellular region of the dressing material will expand and absorb a limited amount of exudate but the dense cellular region will prevent the exudate from passing right through the dressing material.

17. A wound dressing material according to claim 16, wherein said collapsed open cells have substantially the configuration shown in the Figure of the drawing.

18. A wound dressing material according to claim 16, having substantially the configuration shown in the Figure of the drawing.

* * * * *